(12) United States Patent
Wimmer

(10) Patent No.: US 8,066,631 B2
(45) Date of Patent: Nov. 29, 2011

(54) FLEXIBLE ENDOSCOPE WITH LONGITUDINAL AXIAL CHANNELS

(75) Inventor: Viktor Josef Wimmer, Seeon (DE)

(73) Assignee: Karl Storz GmbH & Co. KG (DE)

( * ) Notice: Subject to any disclaimer, the term of this patent is extended or adjusted under 35 U.S.C. 154(b) by 195 days.

(21) Appl. No.: 11/339,255

(22) Filed: Jan. 25, 2006

(65) Prior Publication Data

US 2006/0287572 A1 Dec. 21, 2006

(51) Int. Cl.
*A61B 1/00* (2006.01)

(52) U.S. Cl. .......... 600/107; 600/127; 600/129

(58) Field of Classification Search .......... 600/107, 600/121, 123, 127, 129, 141, 142, 156, 157, 600/139, 104, 137, 106, 124, 146, 153
See application file for complete search history.

(56) References Cited

U.S. PATENT DOCUMENTS

| | | | | |
|---|---|---|---|---|
| 3,915,157 A * | 10/1975 | Mitsui | | 600/107 |
| 3,924,608 A * | 12/1975 | Mitsui | | 600/107 |
| 4,245,624 A * | 1/1981 | Komiya | | 600/106 |
| 4,419,987 A * | 12/1983 | Ogiu | | 600/108 |
| 4,436,087 A * | 3/1984 | Ouchi | | 600/106 |
| 4,452,236 A * | 6/1984 | Utsugi | | 600/107 |
| 4,763,662 A * | 8/1988 | Yokoi | | 600/461 |
| 5,460,168 A * | 10/1995 | Masubuchi et al. | | 600/123 |
| 5,499,630 A * | 3/1996 | Hiki et al. | | 600/461 |
| 5,573,494 A * | 11/1996 | Yabe et al. | | 600/121 |
| 5,575,756 A * | 11/1996 | Karasawa et al. | | 600/157 |
| 5,577,654 A * | 11/1996 | Bishop | | 227/175.1 |
| 5,924,976 A * | 7/1999 | Stelzer et al. | | 600/106 |
| 6,036,636 A * | 3/2000 | Motoki et al. | | 600/146 |
| 6,419,626 B1 * | 7/2002 | Yoon | | 600/109 |
| 6,447,444 B1 * | 9/2002 | Avni et al. | | 600/121 |
| 6,645,140 B2 * | 11/2003 | Brommersma | | 600/128 |
| 6,712,757 B2 * | 3/2004 | Becker et al. | | 600/121 |
| 7,637,905 B2 * | 12/2009 | Saadat et al. | | 606/1 |
| 2001/0053909 A1 * | 12/2001 | Nakada et al. | | 606/47 |
| 2001/0056222 A1 * | 12/2001 | Rudischhauser et al. | | 600/130 |
| 2002/0049367 A1 * | 4/2002 | Irion et al. | | 600/173 |
| 2003/0032860 A1 * | 2/2003 | Avni et al. | | 600/121 |
| 2003/0040657 A1 | 2/2003 | Yamaya et al. | | |
| 2004/0044270 A1 * | 3/2004 | Barry | | 600/142 |

FOREIGN PATENT DOCUMENTS

| | | |
|---|---|---|
| DE | 2429476 | 1/1975 |
| EP | 0 049 851 | 4/1982 |
| WO | WO/0048505 | 8/2000 |

OTHER PUBLICATIONS

PCT International Search Report, Jan. 13, 2005, 3 pages.

* cited by examiner

*Primary Examiner* — John P Leubecker
*Assistant Examiner* — Victoria Chen
(74) *Attorney, Agent, or Firm* — St. Onge Steward Johnston & Reens LLC

(57) ABSTRACT

The invention relates to an endoscope having a bendable guide element, by means of which a tool can be securely guided and simultaneously steered outward into a broad operating area at the head of the endoscope.

8 Claims, 2 Drawing Sheets

FLEXIBLE ENDOSCOPE WITH LONGITUDINAL AXIAL CHANNELS

FIELD OF THE INVENTION

The invention relates to a flexible endoscope with longitudinally axial canals according to the generic terms of Patent Claim 1.

BACKGROUND OF THE INVENTION

The use of endoscopes is well known in medical technology. Endoscopes, essentially configured along a longitudinal direction, are introduced into the human body in order to conduct operations there. Colonoscopes are endoscopes that are used in the intestinal area. The endoscopes in this case, according to the state of the art, have appropriate illuminating and photographic elements in order to be able to report on and monitor sites in the body that are to be treated. Furthermore these known endoscopes have canals, which can be used for irrigating or for inserting tools. Particularly in simple endoscopes, the canals extend to the distal end of the endoscope, which usually is designated as the head. There the canals emerge, preferably on the front side, that is, in the endoscope's longitudinal direction, so that a tool, in particular, that is inserted in the longitudinal direction through a working canal can be pushed out of the head on the front side.

A working canal, through which a tool can be pushed, provides an appropriate guide for the tool in order to be able, with a certain control, to push it out of the head and to insert it there. The disadvantage of this type of endoscopes known in the art is that, as a result of the controlled guidance, only a limited area beyond the front side of the endoscope head can be reached by the tool. It is difficult in particular to move the tool into an area lying to the sides of the longitudinal axis. At a certain distance from a site that is to be worked on (for instance a polyp on the inner wall of the intestine), this site can be surveyed by the "forward looking" optical unit. However, the tool either cannot be moved at all, or can be moved only imprecisely, from the longitudinal direction of the endoscope to the intestinal wall. The area covered by the lens and the area to be worked on are often not identical. The area of application is thereby restricted.

It is therefore the object of the invention to create an endoscope with which various tools can be inserted well in variable spaces simultaneously.

This object is fulfilled through an endoscope according to Claim 1.

SUMMARY OF THE INVENTION

The invention proceeds from the recognition that the tool can be used more flexibly in terms of space and at the same time can be guided well if a part of the working canal that guides the tool is configured with joints in the area of the endoscope head. In particular, the jointed part (which in addition is designated as a guide element) can be rotated about a swivel axis, which runs essentially perpendicular to the longitudinal direction of the endoscope.

According to the invention, the working canal for the tool or tools at first runs along the longitudinal direction of the endoscope. In the head area of the endoscope the working canal, before it emerges at the front side of the endoscope head, runs through the guide element. In the non-rotated position, the last section of the working canal is positioned to be essentially in true alignment with the working canal leading to the proximal end of the endoscope. The distal end of the guide element thus coincides with an imaginary front side that closes off the endoscope head on the distal side. A tool pushed through the working canal of the endoscope and also through the working canal of the guide element then emerges at the front side of the head, so that it can be moved out of or pushed into the working canal in an essentially parallel direction to the longitudinal direction of the endoscope.

According to the possibility of rotating the guide element, as foreseen through this invention, the tool can thus be bent at an angle from the longitudinal direction of the endoscope, so that a lateral area, extending away from the front side and lying in the longitudinal direction, can be processed by the tool. The endoscope is therefore advantageously only restricted essentially to being pushed outward in the longitudinal direction of the endoscope in order to operate in this direction. Rather, by rotating the guide element, it can in addition cover an area that lies essentially diagonally in front of the endoscope head.

According to the invention, it should be possible to make a rotation to one or both sides of an imaginary plane, which extends along the axis of the working canal of the endoscope. In a rotated arrangement the longitudinal axis of the working canal in the endoscope then forms an angle alpha≠180 degrees with the longitudinal axis of the working canal in the guide element.

This increases the range of application considerably, because the tool has access to an additional area on the far side of the front side of the endoscope and in particular to its longitudinal axis. Because of the possibility of rotating the working canal, the optical unit and working canal or instrument canal can be guided separately, so that a relative motion is possible between the optical unit and the last segment of the working canal configured in the guide element. As a result, the area covered by the optical unit and the area reachable by the tool can be advantageously coordinated with one another.

Owing to the configuration of the last segment of the working canal as guide, it becomes possible to have a very precise handling of the tool pushed through the canal. Because this guide surrounds the tool or its shaft on all sides, it can be pressed in a lateral direction and can also be actively rotated again out of this position. Thus, in contrast to the Albarran deflector known in the art, a pulling motion is also possible out of the lateral (deflected) position of the tool back in the direction toward the central longitudinal axis of the endoscope.

An advantageous embodiment of the invention foresees equipping the guide element at its proximal end with appropriate insertion aids, which facilitate pushing a tool through. Thus, unlike in the Albarran deflector, and especially in the angled (rotated outward) position of the guide element, from the proximal end of the endoscope a tool can be pushed through the working canal, which is further threaded into the guide element by means of the insertion aids. A simple insertion aid can be, for instance, a funnel-shaped cavity at the proximal end of the guide element.

A particularly simple embodiment of the invention foresees that the axis of rotation around which the guide element can rotate, is positioned essentially diagonally to the longitudinal axis of the endoscope. This, advantageously, allows the maximum outward steering at a small angle of rotation. The smaller the angle of rotation, the smaller the required manipulation becomes at the proximal end of the endoscope. In the simplified structure, thus, the handling is also facilitated.

An additional advantageous embodiment of the invention foresees that a rigid segment of the head extends as far as the front side, beside the rotatable guide element. Such an area can advantageously make possible additional functions of the endoscope and can be configured, for instance, for inserting working canals and/or optical units and/or media canals and/or as a stop for the guide element (F). The media canals advantageously serve for irrigation or suction.

Such canals can be guided in stable and well-protected fashion as far as the front side of the head, where they emerge (irrigation canals) or are closed off by a lens system (optical system). An additional advantage of such a rigid segment is that the jointed guide element is protected against lateral forces, which could be received by the rigid segment. This makes the guide element, and thus the endoscope head, less sensitive to undesired mechanical impacts and thus increases its lifetime.

An additional embodiment of the invention foresees that at least the non-jointed part of the working canal is configured simultaneously as irrigation or suction canal. Thus it can simultaneously use the guide of the tool and the tubular shape of the canal in order to combine two functions in one canal and thus save space. The jointed segment of the guide canal can—but is not required to—surround the tool so tightly for guide purposes, that the suction is not carried out through this segment but goes past it. The medium to be suctioned streams thus past the guide element and enter the non-jointed part of the working canal, which at the same time functions as a suction canal.

An additional advantageous embodiment of the invention foresees that the rotation motion of the guide element is restricted by at least one stop in at least one rotation direction. Such a stop stabilizes the guide element and prohibits an uncontrolled motion on its part. In particular, the stop can serve as a support against a spring-tensioned forced movement if in particular the guide element can be moved against a spring out of the stopped position or out of another predetermined position. Upon releasing the activation cable (Bowden cable or other operating element) that moves the guide element, this element comes into contact advantageously against the stop, and thus comes into a defined rest position. The operation is made safer and easier to monitor as a result.

The Bowden cable here can work against a pressure spring and/or a cable spring or other appropriate retraction element, so that this element can be positioned in the area of the Bowden cable or else at another site in order to compel a relative movement between rotation element and head.

According to the invention, the activation element, such as a Bowden cable, is guided into a canal and can be removed from the canal for purposes of cleaning or maintenance. The guide element is also positioned especially advantageously to be separable in order better to allow cleaning or maintenance of the endoscope.

Another advantageous configuration is seen in an embodiment of the invention in which the working canal has at its distal (end) segment in the guide element a smaller diameter than in its proximal ("unmoved") segment. Because the proximal segment of the working canal can be used at the same time as irrigation or suction line, a correspondingly increased (ring) gap should be foreseen between the canal wall and the tool guided in the canal. On the other hand the distal ("moved") segment of the working canal in the guide element should primarily serve for more precise guidance of the tool and should therefore surround it as tightly as possible. To maintain a good suction effect, the guide element should be provided with apertures, particularly lengthwise indentations in an essentially axial direction. These indentations on the inside (in the inside wall of the working canal of the guide element) and/or on the outside of the guide element, allow an improved suction performance as far as the distal end of the endoscope, which can be improved further by means of a sheath surrounding the head. The suction effect here can be maintained by the working canal in the guide element and/or around the guide element or passing by it.

The stop can also advantageously be configured by the rigid segment, which extends laterally to the guide element as far as the front side. Also here the guide element, in the unpressed state, can rest laterally on the rigid segment, so that, in comparison with the outward-rotated position, it assumes a more supported position inside and outside the human body.

Additional advantageous embodiments of the invention concern the arrangement of the axis of rotation of the guide element. If, for the last segment of the working canal in the guide element, one defines a working canal axis B' and, in the remaining area of the working canal lying in front of it, a working canal axis B, then the two axes B and B' in the non-outward-rotated position of the guide element are in true alignment. The working canal thus extends through the endoscope head without any bending. In the angled condition, on the other hand, the two axes B and B' form an angle alpha≠180 degrees.

In an advantageous embodiment of the invention, the axis of rotation of the guide element is positioned in the area enclosed by the angle alpha. It can be seen in particular in the description of the illustrations below that in this case the axis of rotation can be positioned in the outer area of the endoscope head. The advantage of this embodiment consists in the fact that the guide element is designed of simple structure and can offer the greatest possible guidance for the tool that is pushed through it. In addition the axis of rotation is more accessible, so that the guide element can be removed more easily for cleaning or maintenance.

In another advantageous embodiment of the invention, the axis of rotation is positioned in the area enclosed by the angle alpha. In this sequence the axis of rotation preferably runs in the inside of the endoscope head, offering the advantage of a better protection from contamination. In addition this case makes possible a structural design of the guide element demanding less material. Moreover, there is the advantage that in the non-outward-rotated position there is, between the guide element and the remainder of the head, an opening angle which, in particular, makes possible cleaning procedures of the working canal or of the last segment of the working canal lying in the guide element. Also, the central arrangement of the axis of rotation in particular makes possible a symmetrical rotation on both sides of the head and thus allows at least partly symmetrical manufacturing geometries.

An additional advantageous embodiment foresees that the proximal restriction of the guide element has two front surfaces that form an angle beta<180 degrees, in whose imaginary cutting area the axis of rotation is positioned in such a way that the front surfaces are configured as stop surfaces that restrict the rotation movement and interact with stop segments of the head. Such a shape allows a bilateral "tipping" of the guide element in relation to an imaginary plane that divides the endoscope in the middle, each extending to a stop, which the front surfaces of the guide element form with surfaces of the head, as will later be seen in particular from FIGS. 3 and 4. The advantage lies in a simple restriction of the angle of rotation, so that a rotation movement on both sides of the imaginary plane is possible because of the angled proximal front side configuration of the guide element.

Depending on the shape and configuration of the front surfaces and the stop surfaces of the head that interact with them, a successive rotation movement becomes possible arising asymmetrically or asymmetrically to the plane. The stop surfaces of the head can be produced at the distal end of the "unmoved" working canal or else by means of a stop acting in the radial direction.

In another advantageous embodiment of the invention the endoscope has a sleeve extending in the longitudinal direction, surrounding the head radially, and open in the distal direction. This sleeve serves to enlarge a suction surface, which usually arises on the front side of a suction canal. The sleeve is insulated in the proximal direction against erroneous flows with or by means of the head, so that between the proximal end of the sleeve and the head no suction losses occur. The suction canal, which can also be configured in particular as a tool canal, exerts its suction effect then at the end of the "firm" working canal, that is, before the transition into the guide element. By means of the sleeve surrounding the head, the suction effect extends that to the entire distal open front side of the sleeve. The suction cross-section as a result is clearly enlarged in comparison with the cross-sections of the conventional suction canals, which extend otherwise as far as the front side of the head. The diminished surface throughput during suction action with the inventive sleeve advantageously reduces or prevents the risk of undesired firm suction on mucous membranes or other vessel walls.

The sleeve can simultaneously be configured as a stop for the guide element. In addition it can serve as securing agent of the guide element to the extent that the guide element, with the sleeve pushed upward, cannot be pulled away from its axis of rotation and thus remains in its desired assembly position. The disassembly of the guide element is correspondingly possible in advantageous advantageous manner, in that at first the sleeve is removed and then the guide element—essentially diagonally to the longitudinal axis of the endoscope—is pulled away from its axis of rotation.

The sleeve can be connected with the head by plugging, screwing, or nesting by means of a releasable or non-releasable connection and thus can allow easy assembly or disassembly.

An additional embodiment of the invention foresees that the guide element (F) is connected with the head (K) by plugging, screwing, or nesting by means of a releasable or non-releasable connection. A releasable, that is removable, connection advantageously facilitates the cleaning or replacement of individual parts in this area, while a non-releasable connection leads to a stable and robust structure.

Additional advantageous embodiments can be seen in the subsidiary claims.

BRIEF DESCRIPTION OF THE DRAWINGS

The following illustrated example aims to explain two embodiments of the invention in exemplary manner.

DETAILED DESCRIPTION OF THE INVENTION

Figure 1:
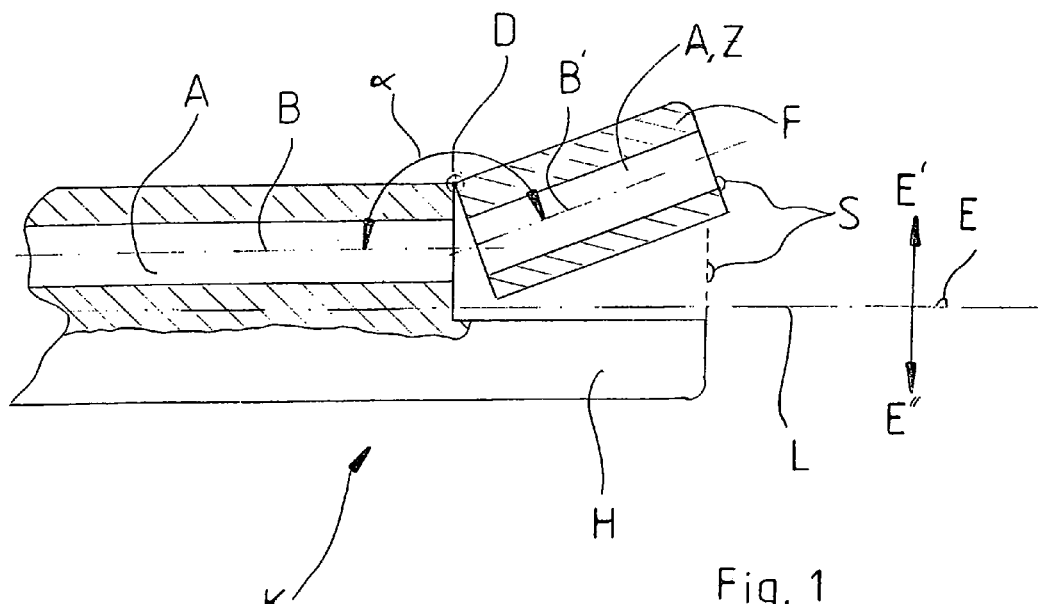
FIG. 1 shows a partial section of a first variant on the endoscope head.

As can be recognized in FIG. 1, an endoscope head K is foreseen which depicts the distal end of an endoscope extending in the illustration from the left.

The head K has a front side S, which encloses the endoscope at the distal end. A part of the head K is a rigid segment H, which extends as far as the front side S. Now shown are various canals and units, which for instance can extend in the rigid segment H as far as the front side (optical systems, irrigation canals, and so on).

The endoscope head is essentially directed along the longitudinal direction L of the endoscope. From the proximal end in the direction toward the viewer, a working canal A extends which is directed essentially parallel to the longitudinal direction L. The working canal A also runs as far as the front side S of the head K, so that a tool pushed through the working canal A can emerge in longitudinal direction from the endoscope head.

In a first segment of the endoscope head K, the working canal A runs along a first canal longitudinal axis B.

In the direction toward the front side S, the endoscope head K has a guide element F. The working canal A is conducted further through the guide element, and in this last segment is designated as Z. The last segment Z of the working canal A runs in the guide element F along a canal longitudinal axis B'.

The guide element F can rotate around an axis of rotation D. In FIG. 1 the axis of rotation D is executed vertically to the sign plane, and thus extends essentially vertically to the longitudinal direction L indicated horizontally in the drawing. The guide element F can rotate around the axis of rotation D in such a way that between the canal longitudinal axes B and B' an angle alpha is enclosed. In the non-rotated position the angle alpha 180 degrees results, so that the canal longitudinal direction B and B' are in true alignment.

If the guide element F is rotated outward out of the aligned position, so that an angle alpha<180 degrees is enclosed by the two canal longitudinal axes B and B', then a tool pushed through the last segment Z is jointed outward from the area of the longitudinal direction L (in the illustrated case, upward). The tool thus gains access to an additional area of the operating site.

Figure 2:
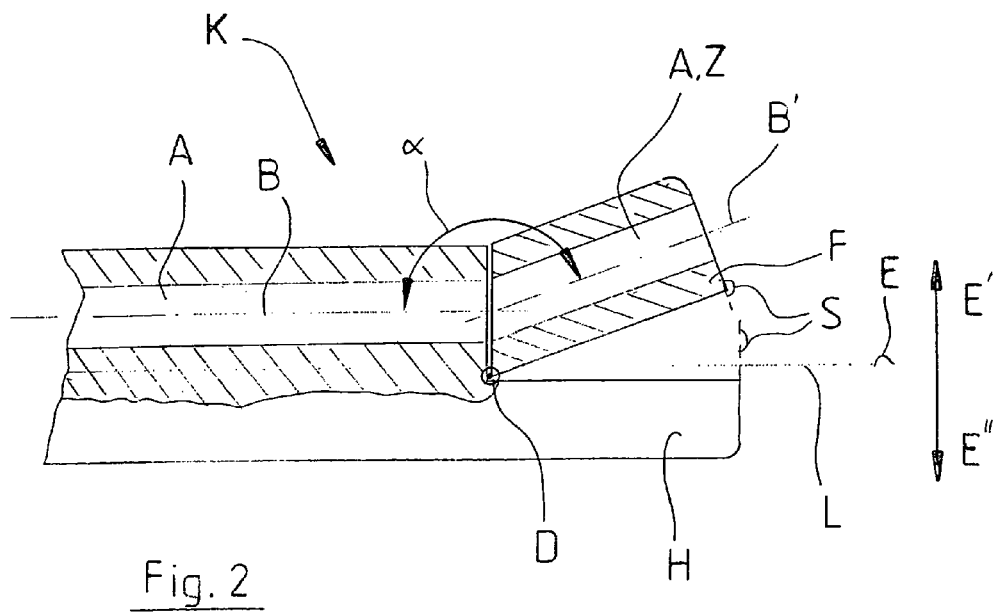
FIG. 2 shows a partial section of a second embodiment variant.

FIG. 2 depicts an endoscope head K identical in extensive sections, in which head the axis of rotation D is positioned elsewhere. The guide element F thus rotates around the axis of rotation D, so that the axis essentially runs through the endoscope head, contrary to an arrangement as in FIG. 1 situated essentially on the periphery of the head.

The guide element F is so tapered in structure in the area in which the canal segment Z passes into the canal segment A, that the rotation movement is possible around a defined mass. Depending on the mass of the tapering here, a stop is thus also defined, which restricts the rotation movement of the guide element F from the longitudinal direction L outward.

An imaginary center plane E along the longitudinal axis L is thus intended to clarify that the guide element F also allows itself to rotate in the direction (not necessarily as far as) the one side E', as in the direction (not necessarily as far as) the other side E".

Figure 3:
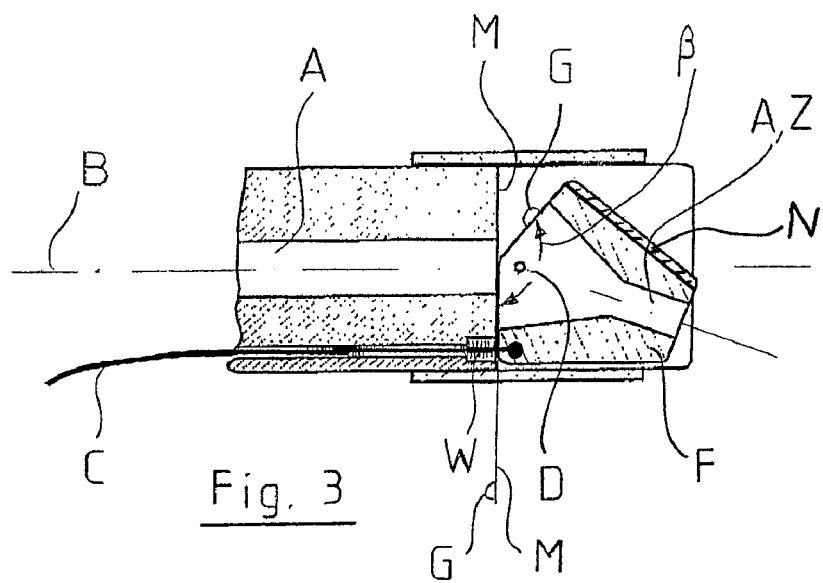
FIG. 3 shows a schematic depiction of an additional embodiment.

FIG. 3 shows a transformed embodiment of an inventive endoscope head. It is possible to make out a working canal A coming from the left, which extends along a canal axis B. The working canal A leads in the head area of the endoscope into guide element F, in whose interior the working canal A is continued further in a final segment Z. The guide element F can rotate around an axis of rotation D.

An activation cable C is coupled on the guide element F coming from the proximal end of the endoscope. The activation cable C can be slid against the force of a spring element W in such a way that the guide element F is rotated around the axis of rotation D.

Figure 4:
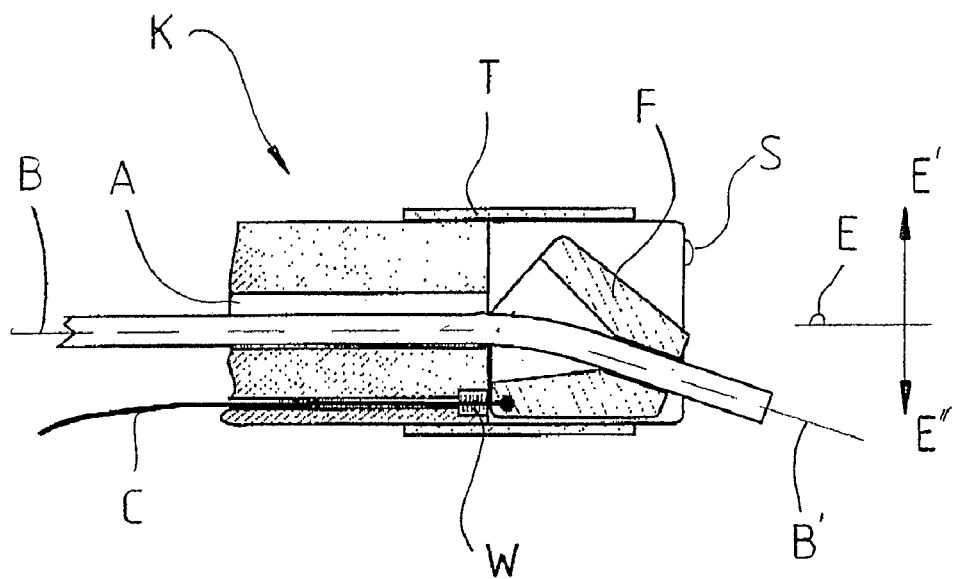
FIG. 4 shows the embodiment in accordance with FIG. 3 with inserted tool.

On its proximal end, the guide element F thus has two front sides G acting as stop surfaces, which define an angle beta, which simultaneously determines the maximum rotation movement of the guide element F around the axis of rotation D. The activation cable C can move the guide element F in such a way that it comes from a first stop position (as depicted in FIGS. 3 and 4) around the axis of rotation D (counter-clockwise and upward in FIGS. 3 and 4) into a second stop position, so that in every stop position one of the front sides G interacts with a stop surface M of the head. In further reference to the FIG. 3, the guide element F, to sustain a suction effect, is configured with openings N, in particular with recesses running in axial direction.

In FIG. 4 the same embodiment is shown, but this time with a tool inserted in the working canal A. The tool extends in the simplified illustration as a tube coming from the proximal end toward the viewer until it goes through guide element F and extends beyond the front side S. As can be seen, the tool is enclosed by this guide element F on all sides, especially in the area of the guide element F, and thus is guided securely. The tool can be pushed in the working canal A or in the guide element F in the longitudinal direction and simultaneously can rotate in the area of the front side S by means of the rotation of the guide element F around the axis of rotation D not shown in FIG. 4 to both sides E' and E" of the plane E.

The head F of the endoscope is surrounded by a sleeve T. The sleeve T on its side pointing to the proximal end of the endoscopes is insulated by the head itself in such a way that between the sleeve T and the head K no medium can flow.

At the opening of the sleeve T of the aperture facing the distal end, however, this aperture is open. The working canal A is simultaneously configured as a suction canal, so that through it, medium can be suctioned in the proximal direction from the head area of the endoscope. The working canal A, which simultaneously is a suction canal, widens at the transition into the guide element F as far as the diameter of the sleeve T. In this way suction can operate over the entire cross-section formed on the distal end by the sleeve T. The sleeve T is thus connected with the endoscope head K, for instance by screwing or plugging.

What is claimed is:

1. A flexible endoscope having a longitudinal axis, a proximal and distal end, and an endoscope head positioned on the distal end, wherein:

the endoscope has at least one working canal for guiding tools and/or operating elements and/or for the through-flowing of media extending toward the distal end and having a working canal longitudinal axis, the working canal longitudinal axis being substantially parallel to the endoscope longitudinal axis;

wherein the head has a guide element having a proximal end and a distal end, the guide element having a guide canal having a guide canal longitudinal axis;

wherein said working canal can rotate in relation to said guide canal around an axis of rotation such that the working canal longitudinal axis and guide canal longitudinal axis can form an angle alpha≠180 degrees;

wherein the proximal end of the guide element has two substantially adjacent front surfaces angled toward the distal end of the guide element forming an angle beta<180 degrees between the two adjacent front surfaces;

wherein the axis of rotation is positioned so that the front surfaces are configured as stop surfaces that restrict the rotational movement of the working canal longitudinal axis relative to the guide canal longitudinal axis by interacting with a stop surface located at a distal end of said working canal and extending in a plane substantially perpendicular to said working canal longitudinal axis;

wherein the endoscope has a sleeve that extends along the working canal longitudinal axis and radially surrounds the head;

wherein the sleeve is open in the distal direction, distinguished in that the distal open end of the sleeve forms a suction opening of the endoscope;

wherein the guide element, for exact guidance of a tool, tightly surrounds the tool, and;

wherein the guide element is configured with one or more recesses extending between said distal end and said proximal end of said guide element along an outer surface of said guide element to sustain a suction effect through said one or more recesses.

2. An endoscope according to claim 1 distinguished in that the rotational movement of the guide element is restricted by at least one stop in at least one rotational direction.

3. An endoscope according to claim 2, distinguished in that the sleeve is insulated in the proximal direction by the head.

4. An endoscope according to claim 2, distinguished in that the sleeve is connected with the head by plugging, screwing, or nesting.

5. An endoscope according to claim 2, distinguished in that the sleeve is configured as a stop for the guide element.

6. An endoscope according to claim 1, distinguished in that the guide element is connected with the head by plugging, screwing, or nesting.

7. An endoscope according to claim 1, distinguished in that the guide element is rotated against the force of a spring element by an activation cable, so that the spring element rotates the guide element in its unactivated state into a predeterminable position.

8. An endoscope according to claim 1, distinguished in that an activation element that moves the guide element can be removed from the endoscope for cleaning and maintenance purposes.

* * * * *

UNITED STATES PATENT AND TRADEMARK OFFICE
CERTIFICATE OF CORRECTION

| | | |
|---|---|---|
| PATENT NO. | : 8,066,631 B2 | Page 1 of 1 |
| APPLICATION NO. | : 11/339255 | |
| DATED | : November 29, 2011 | |
| INVENTOR(S) | : Viktor Josef Wimmer | |

It is certified that error appears in the above-identified patent and that said Letters Patent is hereby corrected as shown below:

Cover Page: Item (63) insert

-- Continuation of application No. PCT/DE2004/001633, filed on July 22, 2004. --

Cover Page: Item (30) insert

-- July 25, 2003  (DE)  103 34 100.5 --

Signed and Sealed this
Thirty-first Day of January, 2012

David J. Kappos
*Director of the United States Patent and Trademark Office*